United States Patent [19]

Apperson et al.

[11] Patent Number: 5,206,511
[45] Date of Patent: Apr. 27, 1993

[54] CALIBRATORS FOR INFRARED-TYPE GAS ANALYZERS

[75] Inventors: Jerry R. Apperson, Seattle; Paul K. Graham, Renton; Leslie E. Mace, Mercer Island; James T. Russell, Bellevue; Lawrence L. Labuda, Issaquah; Walter A. Cooke, Monroe, all of Wash.

[73] Assignee: Cascadia Technology Corporation, Redmond, Wash.

[21] Appl. No.: 600,413

[22] Filed: Oct. 18, 1990

[51] Int. Cl.[5] .............................. G01N 21/61
[52] U.S. Cl. .................... 250/343; 250/252.1; 250/345
[58] Field of Search ............... 250/343, 252.1 A, 345, 250/344

[56] References Cited

U.S. PATENT DOCUMENTS

| | | | |
|---|---|---|---|
| 3,728,540 | 4/1973 | Todd et al. | 250/343 |
| 4,678,914 | 7/1987 | Melrose et al. | 250/343 |
| 4,914,720 | 4/1990 | Knodle et al. | 250/343 |
| 5,013,920 | 5/1991 | Asano et al. | 250/343 |

Primary Examiner—Carolyn E. Fields
Assistant Examiner—Drew A. Dunn
Attorney, Agent, or Firm—Hughes & Multer

[57] ABSTRACT

A method of and device for calibrating infrared radiation transducers. A concentration factor representing the ratio of a data signal to a reference signal for a known concentration of a designated gas in a sample containing that gas is generated. The concentration factor is stored and used during subsequent calibration procedures. The calibration device has a zero cell and a span cell with windows for transmitting infrared radiation and radiation reflecting or absorbing material in the span cell. The span cell therefore provides a known and consistent level of radiation absorption.

23 Claims, 9 Drawing Sheets

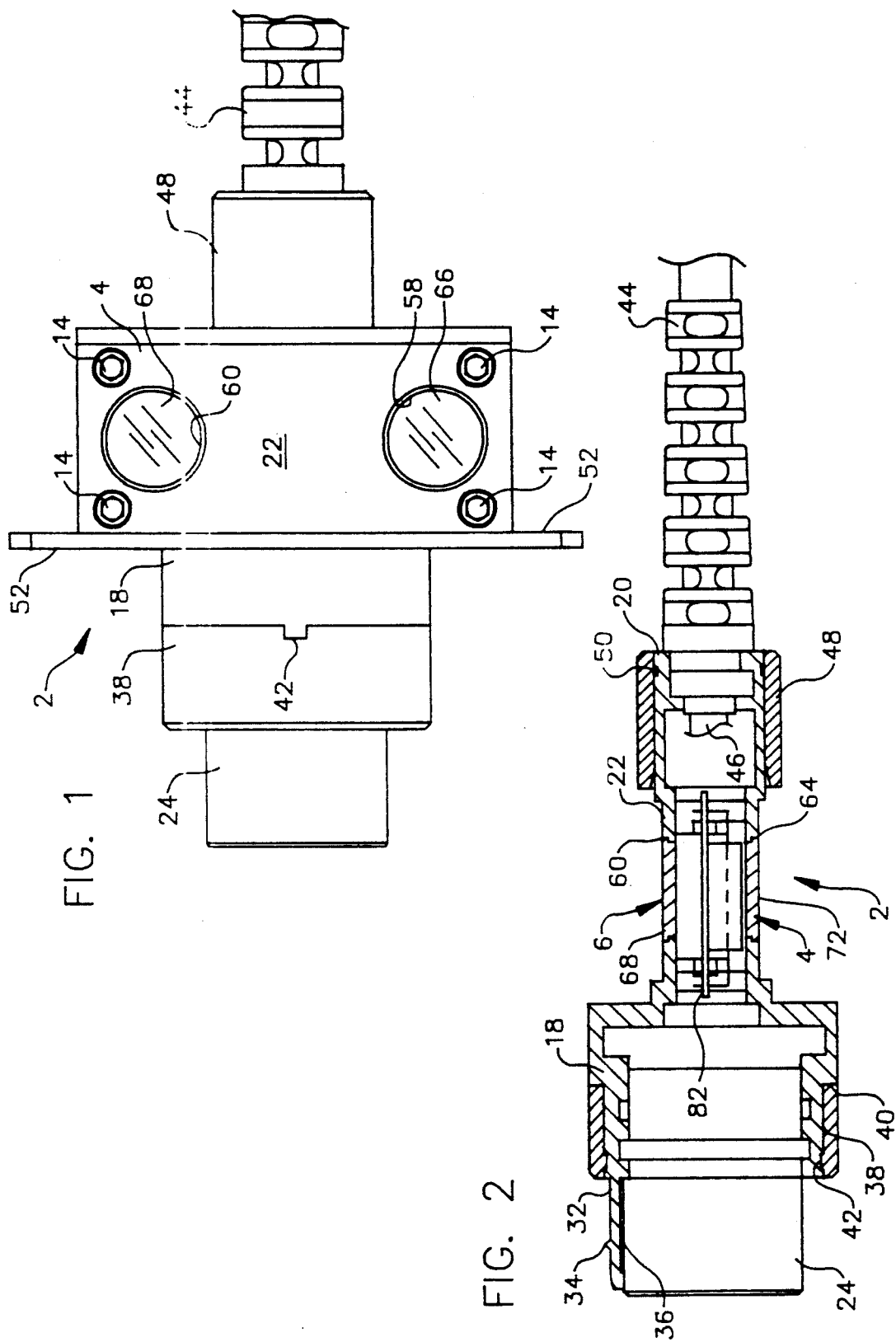

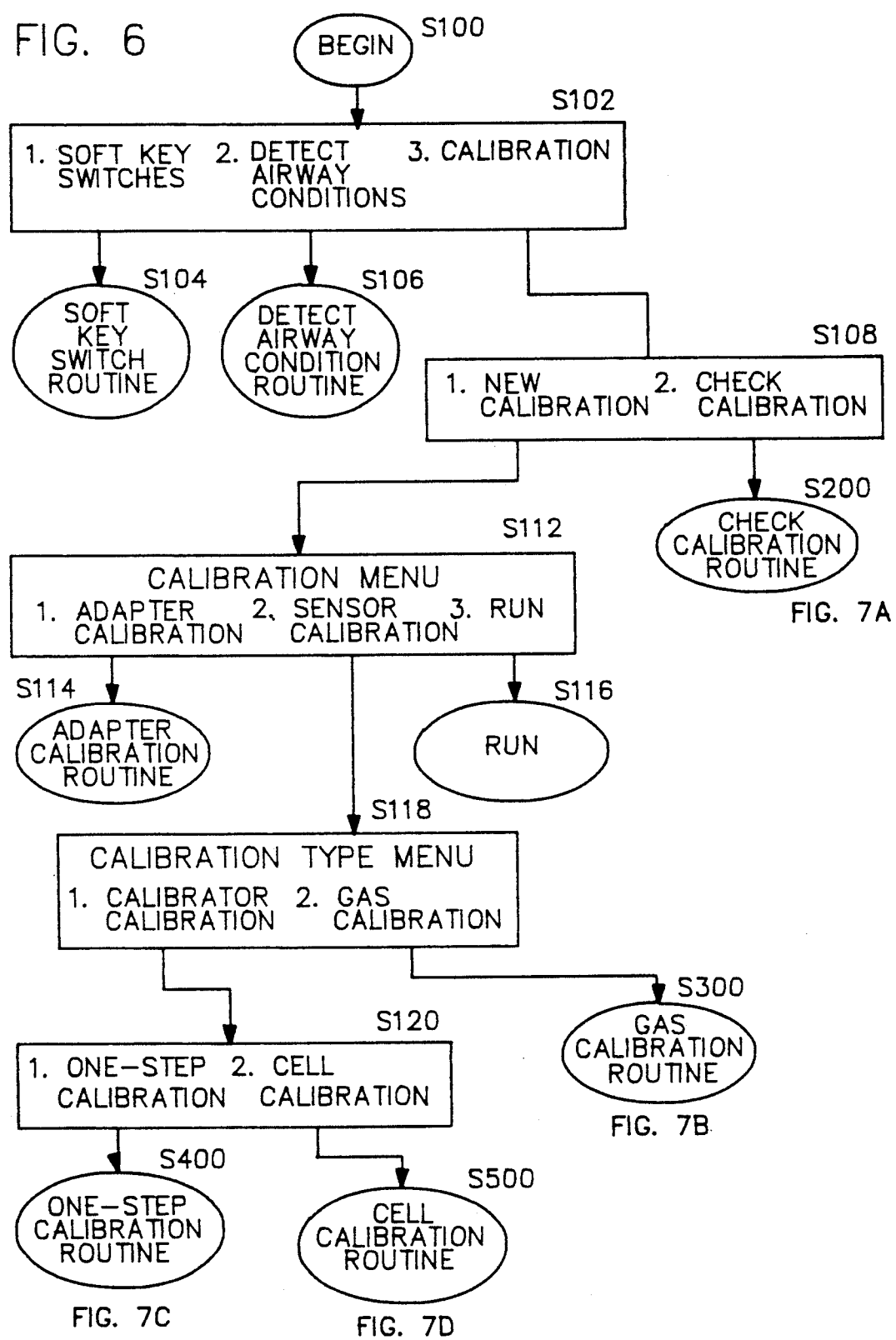

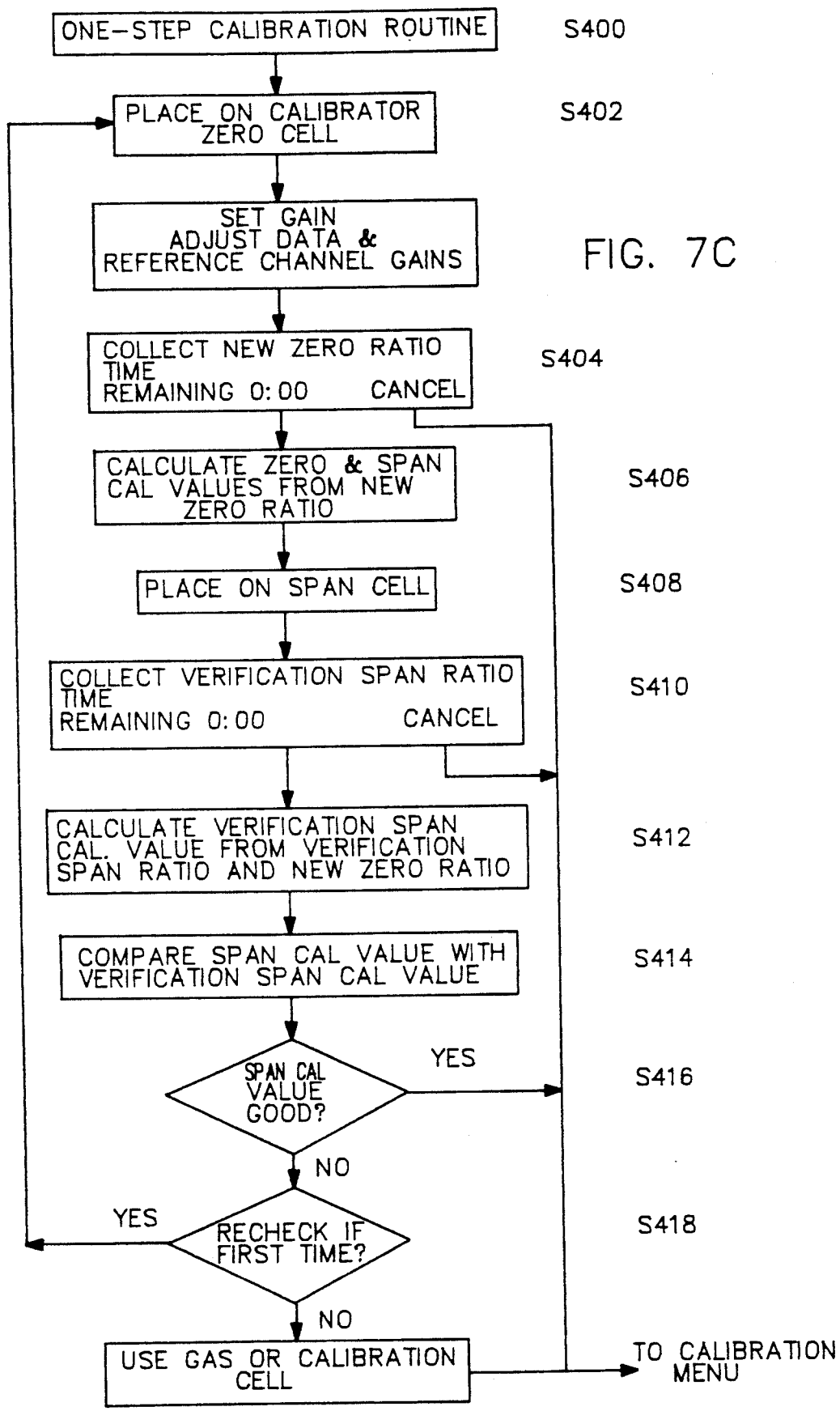

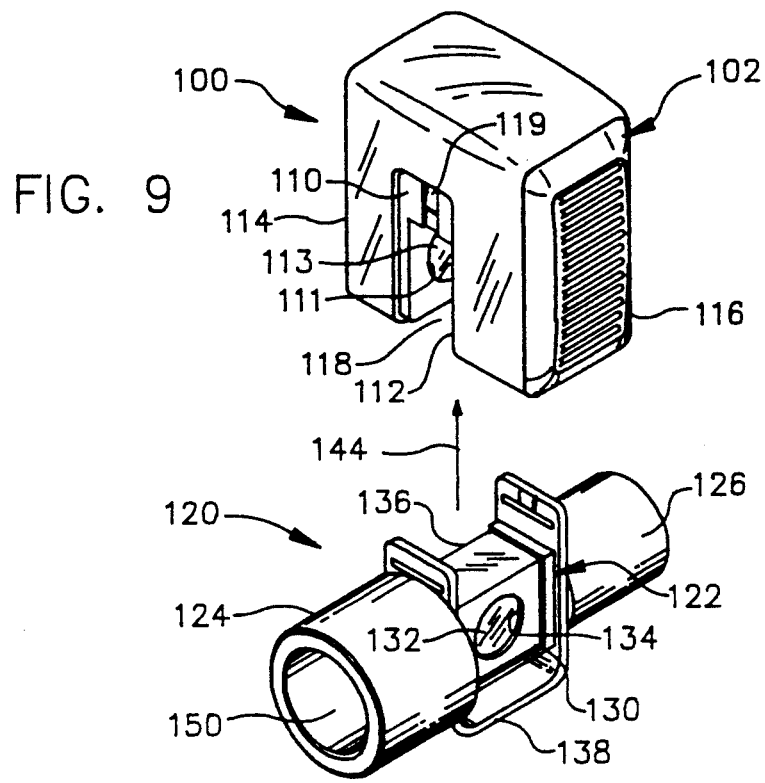
FIG. 9
FIG. 10
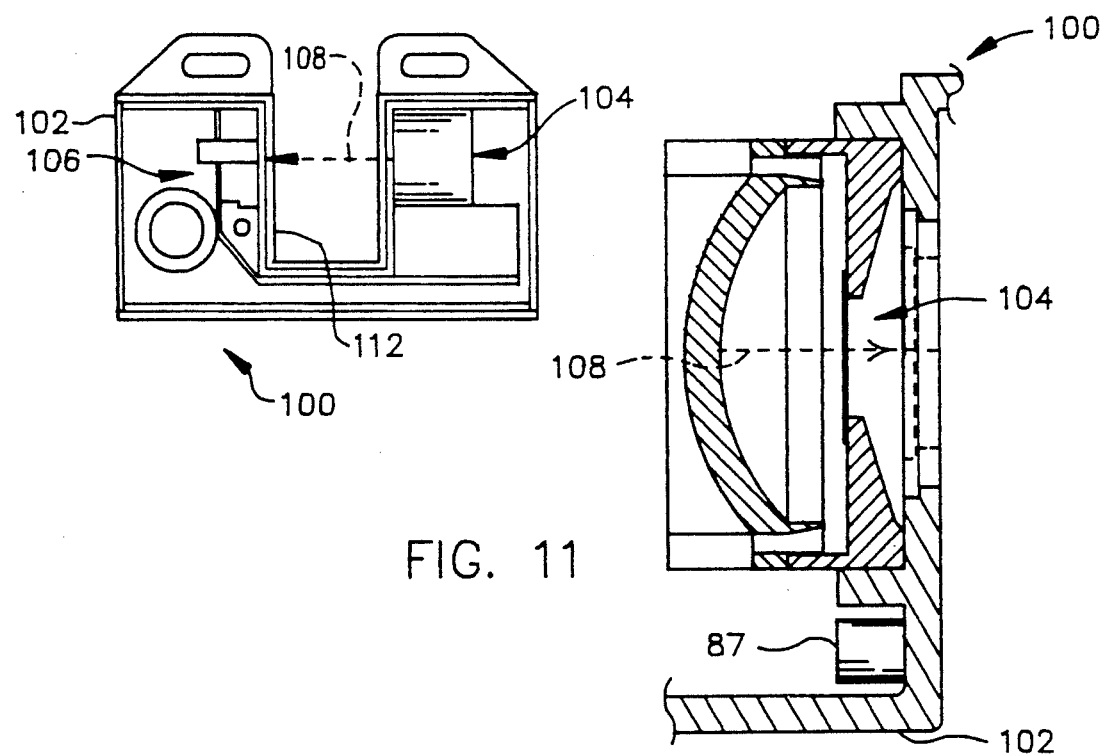
FIG. 11

CALIBRATORS FOR INFRARED-TYPE GAS ANALYZERS

TECHNICAL FIELD OF THE INVENTION

The present invention relates to calibrators and, more specifically, to novel, improved, calibrators for calibrating transducers which have an infrared radiation source and one or more infrared radiation detectors.

BACKGROUND OF THE INVENTION

U.S. Pat. Nos. 4,859,858 and 4,859,859, both entitled "GAS ANALYZER", were issued to Knodle et al on Aug. 22, 1989. Both patents disclose apparatus for outputting a signal indicative of the concentration of a designated gas in a sample being monitored by the apparatus. Apparatus of that character is also disclosed in copending applications Ser. Nos. 07/528,059, filed May 23, 1990, 07/598,984 filed Oct. 17, 1990, and Application No. 07/599,888 filed Oct. 18, 1990, all assigned to the same assignee as the present invention. The gas analyzers disclosed in the '858 and '859 patents and the copending applications are of the non-dispersive infrared radiation (NDIR) type. They operate on the premise that the concentration of a designated gas can be measured by: (1) passing a beam of electromagnetic radiation through the gas, and (2) then ascertaining the attenuated level of the energy in a narrow band absorbable by the designated gas. This is done with a detector capable of generating an electrical output proportional to the amount of energy absorbed by the gas.

One important application of the invention at the present time is in capnometers for monitoring the level of carbon dioxide in the breath of medical patients. This is typically done during a surgical procedure as an indication to the anesthesiologist of the patient's condition, for example. As the patient's wellbeing, and even his life, is at stake, it is of paramount importance that the carbon dioxide concentration be measured with great accuracy.

In a typical instrument or system employing non-dispersive infrared radiation to measure gas concentration, including those disclosed in the '858 and '859 patents and the copending applications, the electromagnetic radiation is emitted from a source and focused by a mirror on the gases being analyzed. After passing through the body of gases along an optical path, the beam of electromagnetic radiation passes through a filter. That filter reflects all of the radiation except for that in the narrow band centered on a frequency which is absorbed by the gas of concern. This narrow band of radiation is transmitted to a detector that is capable of producing an electrical output signal proportional in magnitude to the magnitude of the electromagnetic radiation impinging upon it. Thus, the radiation in the band passed by the filter is attenuated to an extent which is proportional to the concentration of the desired gas. The strength of the signal generated by the detector is consequentially inversely proportional to the concentration of the designated gas and can be inverted to provide a signal indicative of that concentration.

In a typical capnometer, the infrared radiation source and the detector are incorporated into a single transducer. This is assembled to an airway adapter, which is a device with a sampling passage for the gases being monitored.

Most NDIR gas analyzers use a ratioing scheme to eliminate errors attributable to drifts in the infrared radiation source and other parts of the systems and transmission losses. Three methods are common.

1. An optical chopper is used with a single detector. The chopper contains a reference cell or filter, and the detector signal alternates between that reference cell and the gas to be measured. A ratio is taken of these two signals.

2. Two detectors are located next to each other, and each is illuminated by one-half of the infrared radiation beam. A ratio is taken of the detector outputs. The reference channel is presumed to be responsive to any changes in the detected energy that are not due to the absorption of the designated gas, and the changes are presumed to be the same in both the reference and the data channels.

3. A beam splitter is placed in the optical path between a single infrared radiation source and data and reference detectors of like dimension. The radiation is passed through the gases being analyzed and divided by the beam splitter into moieties in which the energy is of wave lengths that are respectively shorter and longer than a designated wave length. The energy in these moieties is transmitted through appropriate band pass filters to the data and reference detectors. A ratio is taken of two detector outputs.

In the third of the foregoing schemes, the actual concentration CONC in *Torrs of a selected gas in the optical path is determined according to the following equations:

$$IX = SCV(ZCV - MR) \quad (1)$$

$$CONC = \text{Table}(IX) \quad (2)$$

In equation (1), IX is an index value, SCV is a Scan Cal Value, ZCV is a Zero Cal Value, and MR is the measured ratio of the data signal to the reference signal. The index value IX is a number used to cross-reference the Measured Ratio MR, after it is adjusted by the Zero and Span Cal Values, to a concentration table containing actual concentrations of a selected gas corresponding to different ratios of data signals to reference signals. The concentration table of Equation (2) is empirically generated by measuring the ratios of data signals to reference signals for different known concentrations of the gas of interest.

The Measured Ratio is the ratio of the signal through data path $S_D$ to the signal through the reference path $S_R$ for a given gas. It is given by the following equation:

$$MR = \frac{S_{D3}}{S_{R3}}\bigg|_{C=C_m} = \frac{G_D}{G_R}[\exp(-kl_{sc}C_m) + L] \quad (3)$$

where $G_D$ is the gain introduced through the data path, $G_R$ is the gain through the reference path, k is the absorption (extinction) coefficient of the designated gas at a specific wave length, $l_{sc}$ is the optical path length of a sample chamber containing the gas of interest, $C_m$ is the measured concentration of the selected gas, and L is the light leakage in the absorption band of the selected gas.

Zero Ratio (ZR) is the ratio of the data signal to the reference signal when the concentration of the gas being measured is zero. The Zero Ratio is given by the following equation:

$$ZR = \frac{G_D}{G_R}(1 + L) \quad (4)$$

The Zero Ratio is measured by placing a sample in which the designated gas is absent in the optical path of the transducer unit and measuring the data and reference signals. While the zero ratio is being calculated, the voltages of the reference and data signals are set as close as possible to the same value using automatic gain control circuitry. The ratio of data to reference signals is thus ideally equal to unity.

For calibration purposes, a Span Ratio (SR) is also employed. The Span Ratio is the ratio of the data signal to the reference signal for a known concentration of selected gas Cs. Substituting the span concentration Cs into equation (3) yields the following equation:

$$SR = \frac{S_D}{S_R}\bigg|_{C=C_S} = \frac{G_D}{G_R}[\exp(-kl_{sc}C_s) + L] \quad (5)$$

The Zero and Scan Cal Values are calculated from the Zero and Span Ratios according to the following equations:

$$ZCV = ZR \quad (6)$$

$$SVC = \frac{IX_S}{ZR - SR} \quad (7)$$

where $IX_S$ is the index value corresponding to the known span concentration level $C_S$.

In one prior method of calibration, known as gas flow calibration, an operator flows a sample in which the gas of interest is absent through an open chamber to obtain a zero ratio ZR. The operator then flows a mixture of the selected gas and another gas through the open chamber and obtains a span ratio SR. The percentage of selected gas in and flow volume of the sample is known; accordingly, the concentration of the sample gas of interest in the sample is known. The zero ratio ZR and span ratio SR thus obtained represent known concentration levels at two points and may be used to calculate Zero and Span Cal Factors according to equations (6) and (7) above.

In a second calibration method, referred to hereinafter as the gas cell method, the transducer analyzer is calibrated using known gas concentration levels of the selected or designated gas in two sealed cells. A first cell, known as the zero cell, does not contain the gas of interest. A second cell, known as the span cell, contains a known concentration of that gas. The operator measures the Zero Ratio by placing the zero cell in the optical path of the detector and the Span Ratio by placing the span cell in the optical path. As in the gas flow calibration method, once two points are known, the Zero and Span Cal Values may be calculated according to equations (6) and (7) above.

Many difficulties are manifest in these two calibration schemes. Both gas flow calibration and gas cell calibration require that two points be measured before the transducer can be calibrated. If the transducer is used to measure the concentration of $CO_2$ exhaled by a patient during an operation, the time involved in measuring two points during calibration may be unacceptable.

Additionally, the following problems are specific to the gas flow calibration method.

It requires that two gas storage tanks be kept available for calibration. One gas storage tank is needed to supply the gas that is not the gas of interest in obtaining the zero ratio, and the other gas storage tank is required to supply the known mixture of the selected gas and the other gas used in obtaining the span ratio. Given the confined spaces of most operating rooms, it may be inconvenient or not feasible to keep two gas storage tanks on hand. The time required to set up a calibration procedure involving flowing two gases through the transducer calibration set-up may also be unacceptable.

Further, in the gas flow calibration method, the flow rate and percentage concentration of the known gas mixture must be carefully regulated to ensure that the actual concentration of the carbon dioxide or other selected gas in the known mixture closely corresponds to the span concentration level used to calculate calibration values. Should the flow rate vary from the desired value, inaccuracies in calculating gas concentrations may result.

The gas cell calibration method also has its own unique problems. The span cell containing the known concentration of the designated gas may leak, rendering the span ratio SR and calibration values calculated therefrom inaccurate. Further, construction of a sealed cell is difficult and expensive.

SUMMARY OF THE INVENTION

There have been invented, and disclosed herein, certain new and novel calibrators that make possible simple, time-efficient, and accurate calibration of infrared radiation/detector transducers.

In the present invention, a Concentration Factor ($CF_s$) is predetermined for a specific transducer analyzer. The Concentration Factor is independent of the gain of the system, requiring only: (a) a specific concentration of the gas of interest, and (b) a sample chamber which can be associated with the transducer being calibrated. The Concentration Factor can be defined as the ratio of the absorption at a given designated gas concentration to the absorption at zero concentration of the designated gas. The Concentration Factor for a specific transducer is stored in non-volatile memory.

The transducer is calibrated in a novel one-step process by obtaining a Zero Ratio, retrieving the Concentration Factor from the non-volatile memory, and calculating Zero and Span Cal Values from the Zero Ratio and the Concentration Factor (hereinafter referred to as the one-step calibration method). The need to measure both Zero and Span Ratios is eliminated.

Since the gains of the data and references channels or detectors are set to approximately the same value by the automatic gain control circuitry, the Span and Measured Ratios are derivable from the Zero Ratio and the Concentration Factor. The following equations define the Measured and Span Ratios in terms of the Concentration Factor and the Zero Ratio:

$$MR = ZR(CF_m) = \frac{[G_D(1+L)][\exp(-kl_{sc}C_m) + L]}{[G_R][1+L]} \quad (8)$$

$$SR = ZR(CF_s) = \frac{[G_D(1+L)][\exp(-kl_{sc}C_s) + L]}{[G_R][1+L]} \quad (9)$$

The closer the automatic gain control sets the gain of the data and reference channels to equal, the closer the Span and Measured Ratios are to the absorption term. Accordingly, a linear relationship exists between the Measured Ratio and the absorption term. However, the relationship between the Measured Ratio and the sample gas concentration C is exponential.

In the foregoing equations, k is constant for a given sample gas, $1_{sc}$ is constant for all airway adapters and the calibrator being used, and L is fixed by the amount of light passing through the filter. Therefore, the Concentration Factor $CF_s$ for a given span concentration level $C_s$ is constant.

Therefore, once the gains in the system are set on zero percentage concentration of the designated gas, the known Concentration Factor for a selected gas may be used to calculate the Span Cal Value.

The Concentration Factor may be carried in non-volatile memory in two ways. First, the concentration factor may be calculated in the factory from equation (9) for a given Zero Ratio. and Span Ratio. During subsequent factory or field calibration of a specific transducer a New Zero Ratio (NZR) is measured; and a New Span Ratio (NSR) for the transducer calibration is calculated according to the following equation:

$$NSR = NZR \, (CF_s) \qquad (10)$$

The second method of carrying the Concentration Factor is to store Zero and Span Ratios calculated at the factory and calculate a New Zero Ratio and New Span Ratio therefrom for a specific transducer being calibrated according to the following equations:

$$NSR = NZR \cdot \frac{SR}{ZR} \qquad (11)$$

The New Zero and Span Ratios are then substituted for the Zero and Span Ratio terms, respectively, in equations (6) and (7) to solve for the Zero and Span Cal Values.

The novel method of calibrating infrared radiation transducers disclosed herein is superior to the prior gas flow and gas cell methods because:

(a) The Span Ratio can be readily calculated for a specific transducer from a Concentration Factor determined under carefully controlled factory calibration procedures;

(b) two measurement points are not needed;

(c) gas storage tanks need not be kept on hand; and (d) the expense and uncertainty of sealing a known concentration of the gas of interest in a span cell is avoided.

Also disclosed in this specification is a novel, non-gas absorption type span cell for checking the calibration obtained in the one-step process described above or to be used as a calibration cell in a two step process. That cell includes a window having a radiation reflecting film formed thereon. When the span cell is placed in the optical path of an infrared radiation transducer, the film reflects an amount of radiation which is the same as the amount of radiation absorbed by a specific concentration of the gas of interest. The non-gas absorption span cell thus provides radiation reflection that corresponds to the absorption of a known concentration of the selected gas without a sealed cell.

Calibration devices employing both zero and span cells have magnetic reed switches, one corresponding to each of the zero and span cells. The zero cell magnetic reed switch is located adjacent the zero cell, while the span cell magnetic reed switch is located adjacent the span cell. When one of the zero or span cells is placed in the optical path of the detectors in a transducer being calibrated, the appropriate reed switch is closed by a magnet component of the transducer. Accordingly, because the calibrator then knows which cell is placed in the optical path during calibration, improper calibration due to operator error in identifying the cell placed in the optical path is avoided.

A further novel feature of the present invention is that the non-volatile memory containing the Concentration Factor may be physically attached to the transducer unit for which the Concentration Factor is calculated. The memory may be located within: (a) the transducer housing, or (b) the calibrator unit containing the zero and span cells with the calibrator unit being physically connected to the transducer. A particularly advantageous arrangement is to locate the non-volatile memory in the calibrator unit and attach the calibrator unit to a cable running from the transducer detector to the gas analyzer or other apparatus in which the transducer is incorporated. In this arrangement, the non-volatile memory may be electrically connected to the transducer; and the gas analyzer through the calibrator unit, allowing transfers of information among the transducer, the non-volatile memory, and the gas analyzer.

The present invention may be configured to allow use of the heretofore employed gas flow and gas cell calibration methods, in addition to the one-step or two-step calibration method of the present invention. Thus, any appropriate method of calibration may be chosen, and maximum flexibility in calibrating infrared radiation transducers for NDIR gas analyzers and other apparatus is maintained.

OBJECTS OF THE INVENTION

From the foregoing, it will be apparent that one important and primary object of the present invention is to provide novel calibrating methods and calibrators for infrared radiation transducers.

Further objects of the invention reside in the provision of methods and devices as characterized in the preceding object that:

are particularly useful in calibrating those infrared radiation transducers that generate both a reference signal and a data signal indicative of the concentration of a selected gas in a sample being analyzed;

are compact and rugged and therefore particularly well suited for field use in medical and other demanding applications;

require only one step to obtain a complete and accurate calibration of an infrared radiation transducer;

provide higher accuracy because a span ratio corresponding to a known span concentration level of a selected gas is calculated once under carefully controlled conditions and stored for subsequent use in calculating calibration values;

do not require bulky and inconvenient gas storage tanks;

provide higher accuracy because only one data point need be measured to obtain an accurate calibration;

allow accurate calibration of infrared radiation transducers without the supply of a known concentration of the gas of interest;

provide improved accuracy by generating a concentration factor specific to each transducer;

do not require sealed gas cells for calibration;

provide a non-volatile memory for storing a concentration factor associated with each given transducer;

provide a span cell with absorption properties equivalent to those of a known concentration of a selected gas that can be used as a calibration check or in a two-step calibration method;

allow verification of calibration values by calculating a value corresponding to the absorption through a span cell;

can be used in a variety of applications and to calibrate systems that monitor the concentration of many different gases;

can advantageously be employed in conjunction with an airway adapter to insure accurate measurement of the concentration of a selected gas flowing through the adapter;

allow prior calibrating methods, such as the gas flow and gas cell calibrating methods, to be used instead of the novel one-step calibrating method of the present invention;

provide automatic detection of a zero cell or a span cell placed in the optical path of a transducer; and allow additional information such as a serial number of a transducer to be stored in the non-volatile memory associated with the transducer.

Other important objects and features and additional advantages of the invention will be apparent to the reader from the foregoing, the following description and discussion of the invention, the accompanying drawings, and the appended claims.

BRIEF DESCRIPTION OF THE DRAWINGS

In the drawings:

FIG. 1 is a side view of a calibrator unit having a span cell and a zero cell, either of which can be inserted into an optical path of a transducer being calibrated, the calibrator unit and cells being constructed in accord with the principles of the present invention;

FIG. 2 is a top view of the calibrator unit with its casing cut away to show: (a) the opposing relationship of two windows of one of the cells of the calibrator unit, and (b) a printed circuit board incorporated in the calibrator unit;

FIG. 6 is a flow chart of a MAIN PROGRAM for calibrating infrared radiation transducers in accord with the principles of the present invention;

FIG. 7C is a flow chart of a ONE-STEP CALIBRATION PROCEDURE for implementing the principles of the present invention;

FIG. 9 is an exploded view of: (a) an airway adapter providing a flow path for a gas being analyzed, and (b) an infrared radiation transducer that outputs a signal indicative of the concentration of the designated gas as it flows through the airway adapter.

FIG. 10 is a vertical section through the transducer; and

FIG. 11 is a section through the left-hand end section of the transducer casing supplied to show certain components of the transducer housed in that end section.

DETAILED DESCRIPTION OF THE INVENTION

Figure 3:
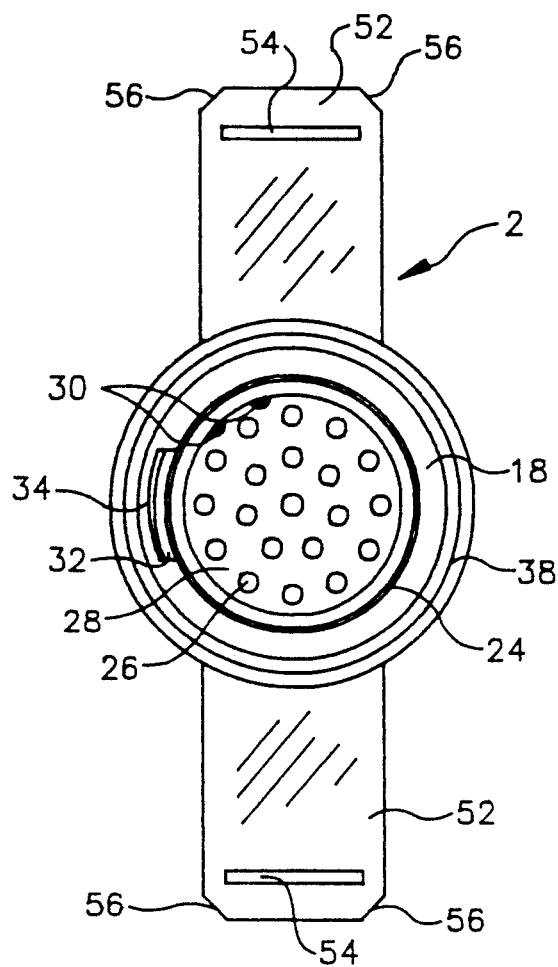
FIG. 3 is an end view of the calibrator unit.

The principles of the present invention can be employed to particular advantage in transducers for outputting: (a) a signal proportional in magnitude to the concentration of carbon dioxide flowing through an airway adapter in a patient-to-mechanical ventilator circuit, and (b) a reference signal. These signals are ratioed in the manner disclosed in the above-incorporated '858 and '859 patents and the cited copending applications to provide a third signal accurately and dynamically representing the concentration of the carbon dioxide flowing through the airway adapter. A representative and preferred calibrator unit constructed in accord with, and embodying, the principles of the present invention is shown in FIGS. 1-5 and identified by reference character 2.

Figure 4:
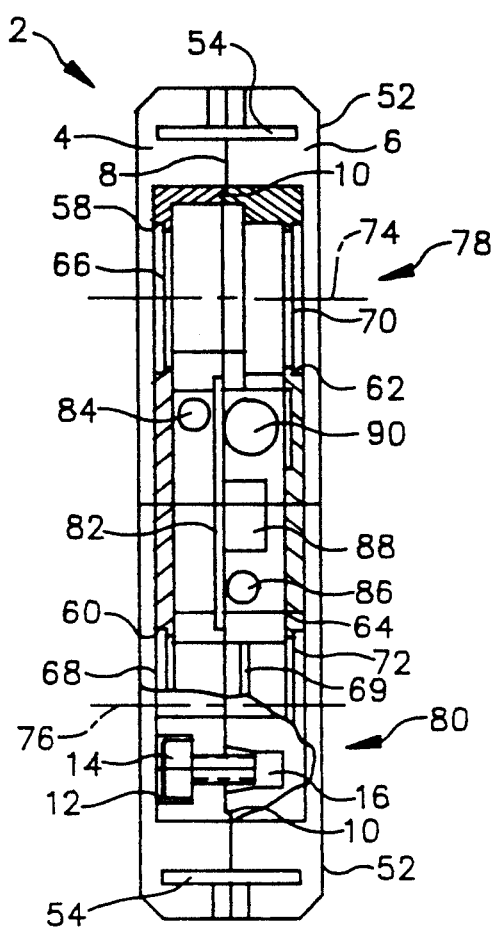
FIG. 4 is a left-hand end view of the calibrator unit with part of the calibrator unit casing broken away to show its internal components.

As shown in FIG. 4, calibrator unit 2 comprises a first part 4 and a second part 6 joined in a substantially clamshell-like arrangement along a seam 8. First part 4 and second part 6 of the calibrator unit 2 are constructed in a substantially symmetrical, mirror-image, arrangement, except that: (a) a groove and mating projection, indicated by reference character 10, are formed on first part 4 and second part 6, respectively, along seam 8, and (b) a recess 12 is formed in the first part 4 for the head of a screw 14, while second part 6 contains threaded holes 16 which are adapted to receive a threaded end of screw 14.

Referring now to FIG. 2, generally cylindrical end portions 18 and 20 of calibrator unit 2 extend from a parallelpipedal middle portion 22. End portions 18 and 20 share a common axis, referred to hereinafter as the chord axis; and the diameter of end portion 18 is greater than the diameter of end portion 20. Middle portion 22 is substantially symmetrical about the chord axis.

The inner surface of end portion 18 is adapted to receive a cylindrically-shaped connector 24 in coaxial relationship to the chord axis. As shown in FIG. 3, connector pins 26 extend from a disk shaped surface 28 of connector 24. The axes of connector pins 26 are parallel to the chord axis. Keying projections 30, the purpose of which will be explained below, extend toward the chord axis from the inner surface of connector 24.

Connector 24 is designed to be matingly received in a corresponding female connector mounted on a gas analyzer control unit (not shown in the drawing). Holes having a grouping similar to that of connector pins 26 are formed in the female connector. Further, keying grooves are formed on the female connector; these are adapted to receive keying projections formed on connector 24. Accordingly, when male connector 24 engages the female connector, keying projections 30 ensure that connector pins 26 are received in their corresponding connector holes of the female connector-in a predetermined and consistent relationship.

Further, an arcuate projection 32, the inner surface of which conforms to the outer surface of connector 24, extends from end portion 18 parallel to the chord axis.

Arcuate projection 32 contains an annular locking projection that radially projects from the outer surface of arcuate projection 32 and is generally perpendicular to the chord axis.

When connector 24 is mated with the corresponding female connector of the gas analyzer control unit, arcuate projection 32 penetrates a similarly shaped arcuate groove formed around the female connector. Locking projection 34 contacts the arcuate groove of the female connector and depresses arcuate projection 32 into a gap 36 between the arcuate projection 32 and connector 24. Locking projection 34 positively mates with a similarly shaped annular groove of the female connector to lock the male connector 24 into the female connector when the male connector 24 is fully inserted. Arcuate projection 32 may be depressed toward gap 36 to release locking projection 34 to remove connector 24 from the female connector.

A polymeric barrel 38 securely fits into an annular notch 40 formed on the outer surface of end portion 18. An annular notch and groove arrangement 42 securely locks barrel 38 into notch 40. Barrel 38 prevents separation of first part 4 from second part 6 of the calibrator unit 2 at end portion 18.

The inner surface of end portion 20 is adapted to receive a strain relief member 44 which surrounds an external cable 46. Strain relief member 44 is well-known in the art and will not be discussed further.

Cable 46 contains a plurality of conductive wires and will be discussed in further detail below.

The inner surface of a barrel 48 is designed to conform to the outer surface of calibrator unit end portion 20. An annular notch and groove arrangement 50 formed between end portion 20 and barrel 48 locks barrel 48 onto end portion 20. Barrel 48 prevents separation of first part 4 and second part 6 of calibrator unit 2 at the end portion.

Calibrator unit middle portion 22 has flanges 52 radially extending therefrom. Slots 54 are formed in the distal ends of flanges 52. Bevelled edges 56 are also formed on the distal ends of flanges 52. The purpose of slots 54 and bevelled edges 56 will be discussed below.

Apertures 58 and 60 are formed on first part 4 of calibrator unit 2. Apertures 62 and 64 are formed on the second part 6 of the calibrator unit 2. Apertures 58, 60, 62, and 64 are substantially circular and have diameters determined by the optical path of a transducer 100, which will be discussed in detail below with reference to FIG. 9.

The apertures on each part of calibrator unit 2 are symmetrically formed about the chord axis. Further, apertures 58 and 62 face each other and share a common axis, hereinafter referred to as the zero axis. Similarly, apertures 60 and 64 face each other and share another common axis, hereinafter referred to as the span axis. The zero and span axes are transverse to the chord axis.

Windows 66, 68, 70 and 72 are attached to the cell casing and cover apertures 58, 60, 62, and 64, respectively. A zero cell optical path, indicated generally by reference character 74, extends between window 66 and window 70; and a span optical path 76 extends between windows 68 and 72. Windows 66 and 70 and the zero optical path 74 together form a cell 78, hereinafter referred to as the zero cell. Windows 68 and 72 and optical path 76 similarly form a cell 80, hereinafter referred to as the span cell. Zero optical path 74 is coaxial with the zero axis, and the span optical path 76 is coaxial with the span axis.

Calibrator unit 2 is sealed to keep foreign material from the interior of the calibrator unit 2. Care is also taken to prevent measurable quantities of the gas being analyzed from being sealed in the calibrator unit 2.

Windows 66, 68, 70 and 72 are made of sapphire. Sapphire windows do not absorb radiation to an extent that would significantly affect a beam passing through the windows.

Windows 68 and 72 of span cell 80, however, have an infrared radiation reflecting film formed on the inner, facing surfaces thereof. Alternatively, a radiation absorbing disk 69, made from a material such as quartz, can be placed between two transparent windows 68 and 72. The radiation reflecting film formed on windows 68 and/or 72 or, alternatively, the radiation absorbing disk 69, have two general functions: (a) the films reflect or the disk absorbs a known amount of infrared radiation corresponding to the absorption of a known concentration of designated gas, and (b) the radiation absorption films add color to windows 68 and/or 72, enabling the user of the calibrating device to differentiate the opaque span cell from the transparent zero cell.

The reflecting film can be deposited by using standard thin optical film deposition methods. The reflecting film is designed to pass a known percentage of energy above a predetermined wavelength and another percentage below that wavelength. The thickness of the disk is so chosen as to accomplish the same thing. The ratio of the energy above the predetermined wavelength to the energy below the predetermined wavelength is equivalent to a ratio of the data detector to reference detector signals for a known concentration of $CO_2$. For example, passing 88%±2% of the energy above 4 microns and 34%±2% of the energy below 4 microns in a given setting results in attenuation equivalent to a 55 Torr concentration of $CO_2$.

Figure 5:
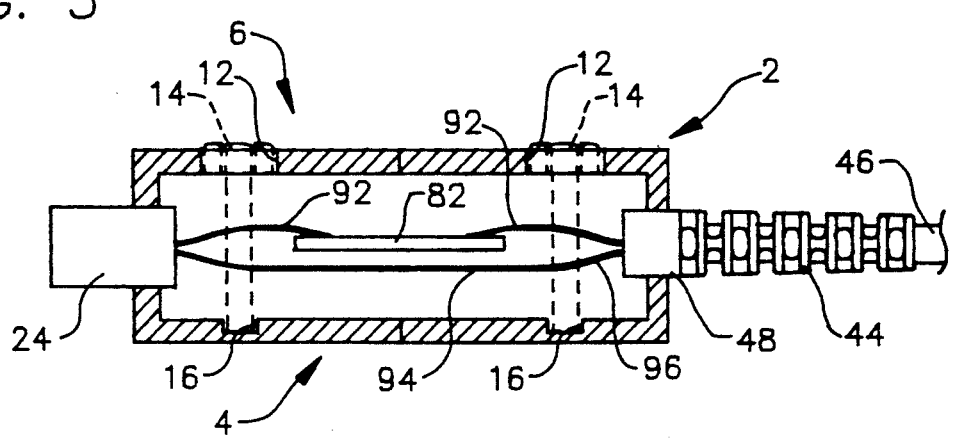
FIG. 5 is a fragmentary, bottom view of the calibrator unit showing certain connections to the printed circuit board component of the calibrator unit.

As shown in FIGS. 2, 4 and 5, calibrator unit 2 further contains a printed circuit board 82. A zero reed switch 84 is located on one side of printed circuit board 82, while a span reed switch 86 is fixed to the other side of printed circuit board 82. Zero reed switch 84 (S1) closes when it is in a proximal relationship to a magnet 87 mounted in the housing of a transducer 100 which includes the detector being calibrated (see FIG. 11). Similarly, span reed switch 86 (S2) is closed when it is placed in a substantially proximal relationship to the switch operating magnet 87 in a transducer being calibrated. The effect of the closing of reed switches 84 and 86 will be discussed in further detail with reference to FIG. 8.

Indicated by reference character 88 is a memory device for storing various parameters and other information concerning transducer 100. Associated with memory device 88 is a battery 90 for maintaining power to memory device 88 when connector 24, the usual source of power to printed circuit board 82, is removed from the female connector on the gas analyzer or other calibration controlling unit. This memory device 88 may be any standard random access memory (RAM) that allows data stored therein to be changed when necessary and held in memory as long as power is supplied to the memory device 88.

Alternatively, memory device 88 may be an electrically erasable programmable read only memory (EEPROM). If an EEPROM device is used instead of standard RAM memory, battery 90 may be dispensed with.

As is apparent from FIG. 4, printed circuit board 82, including all the devices attached thereto, does not extend into or otherwise block the optical path of zero cell 78 or span cell 80. This is accomplished by mounting printed circuit board 82 parallel to the chord axis of calibrator unit 2 and perpendicular to the zero optical path 74 and span optical path 76.

The memory device 88 may alternatively be mounted in transducer casing 102. Or memory device 88 can be located in the gas analyzer or other controlling unit with which the transducer 100 being calibrated is associated. In that case, the user is prompted to identify the serial number of the detector to be calibrated, and the data is recalled from the system-associated memory as required for the thus identified transducer to be calibrated.

In any event, the important result to be achieved is that information specific to a particular transducer 100 be stored in non-volatile memory so that it can be recalled for use during calibration of the transducer.

In contrast, reed switches 84 and 86 must be located within calibrator unit 2 adjacent their corresponding cells 78 and 80 so that the switches will open and close as appropriate.

FIG. 5 schematically shows the routing of the conductive wires 96 in external cable 46 through calibrator unit 2. Conductive wires 96 are divided into a board group 92 and a connector group 94. The signals and voltage supplies carried on the conductive wires of board group 92 are made avaiable to the components mounted on printed circuit board 82. Connector group 94 bypasses board 82 and leads directly to connector 24. The signals contained on the conductive wires of cable group 94 are not accessible to PC (printed circuit) board 82.

As a result, a gas analyzer unit or other system is electrically connected through connector 24 to PC board 82 through the board group 92. The gas analyzer or other unit is also electrically connected via connector 24 to transducer 100 both: (a) directly through connector group 94, and (b) indirectly through board group 92 and PC board 82. Signals may thus be routed among the gas analyzer unit, the PC board 82, and transducer 100.

While not explicitly shown in FIG. 5, it should be apparent from the above discussion that the conductive wires in board group 92 and connector group 94 are arranged so that they will not block the optical paths 74 and 76 through span and zero cells 78 and 80.

Referring now to FIGS. 9-11, reference character 100 of course identifies the transducer which is to be calibrated, and reference character 120 identifies an airway adapter through which the gases that are to be monitored flow. Transducer 100 and airway adapter 120 are not by themselves part of the present invention and will be discussed herein only to the extent necessary for an understanding of the present invention.

Transducer 100 includes the aforementioned casing 102 and switch-operating magnet 87, an infrared radiation source 104, and a unit 106 with lead selenide or comparable infrared radiation detectors, referred to herein as a data detector and a reference detector.

In an exemplary application of the airway adapter and transducer disclosed herein, a gas analyzer (not shown) is employed to measure the expired carbon dioxide level of a medical patient. This expired carbon dioxide level can be employed by medical personnel to control the operation of a mechanical ventilator hooked up to the patient to assist him in breathing. In certain major surgical procedures, the ventilator completely takes over the breathing function for the patient.

In this application of the invention, airway adapter 120 is employed to connect an endotracheal tube inserted into the patient's trachea to the plumbing of a mechanical ventilator. The airway adapter also confines the expired gases to a flow path with a precise, transverse dimension. The flow path is traversed by an optical path 108 between the infrared radiation source 104 and the detector unit 106 in transducer 100.

The infrared radiation emitted from source 104 transverses the gases in airway adapter 120 where it is attenuated by the designated gas in the gases being analyzed. The attenuated beam of infrared radiation is then filtered to eliminate energy of frequencies lying outside a narrow band which is absorbed by the gas being measured. The remaining infrared radiation in that band impinges upon the data detector in detector unit 106. The data detector thereupon generates an electrical signal proportional in magnitude to the intensity of the infrared radiation impinging upon it. That signal is converted to one indicative of the concentration of carbon dioxide in the patient's exhalations. Additional information may also be extracted from the detector-generated signal. This includes minimum inspired carbon dioxide, respiration rate, and end tidal carbon dioxide.

Energy in a second, adjacent band is intercepted by the reference detector in unit 106. The signal consequently outputted by the reference detector is ratioed with that outputted by the data detector to minimize inaccuracies attributable to such anomalies as foreign matter in the optical path 108 between the infrared radiation source 104 and the detectors in detector unit 106.

The polymeric housing 102 of transducer 100 is generally U-shaped and has first and second end sections 114 and 116, respectively, with a rectangularly configured gap 118 therebetween. Left-hand end section 114 houses infrared radiation source 104, and right-hand end section 106 houses detector unit 106.

An optically transparent window 113 covers an aperture 111 in the inner end wall 110 of detector housing end section 114. A second aperture (not shown) is formed in inner end wall 112 of right-hand end section 116 and covered with a second optically transparent window. The transparent windows are generally circular in shape and have a common axis of alignment.

The infrared radiation source 104 in transducer casing end section 114 generates infrared radiation and propagates a beam of that radiation along optical path 108 to the second end section 116 where the beam is intercepted by the data and reference detectors in the detector unit 106 housed in end section 116. The windows in transducer casing 102 offer minimal resistance to the infrared radiation as it transverses path 108.

The detectors generate: (a) a reference signal ($S_R$) corresponding to the magnitude of the unattenuated infrared radiation beam and (b) a data signal ($S_D$) corresponding to the magnitude of that beam after the beam has been attenuated by the designated gas. These two signals are amplified and sent through cable 46 to the gas analyzer (or other unit or system) in which transducer 100 is employed.

The illustrated airway adapter 120 is designed for connection between an endotracheal tube inserted in a patient's trachea and the plumbing of a mechanical ventilator.

Airway adapter 120 is typically molded from Valox polyester or a comparable polymer. Airway adapter 120 has a generally parallelpipedal center section 122 and two cylindrical end sections 124 and 126. A sampling passage 150 extends from end to end through the adapter.

The central section 122 of airway adapter 120 provides a seat for transducer 100. An integral, U-shaped component 138 positively locates transducer 100 endwise of the adapter, and, also, in that transverse direction indicated by arrow 144.

An aperture 134 is formed through wall 130 of airway adapter center section 122 on one side of sampling passage 150. A similar aperture (not shown) is formed in wall 136 of center portion 122 on the opposite side of the sampling passage. These apertures are circular in shape and aligned along a common axis, hereinafter referred to as the airway axis. Aperture 134 is sealed by a sapphire window 132. The aperture in wall 136 is similarly sealed with a sapphire window (not shown).

With airway adapter 120 displaced in the direction indicated by arrow 144 and assembled to transducer 100, sections 114 and 116 of transducer housing 102 embrace the two side walls 130 and 136 of airway adapter center portion 122. So assembled, the apertures in the transducer housing align with the apertures in the center section 122 of airway adapter 120 along optical path 108, allowing infrared radiation to pass without substantial impediment along the optical path from source 104 to detector unit 106.

First and second transducer casing end sections 114 and 116 are also designed to embrace the distal ends of the center section 22 of calibrator unit 2. When so embraced, either the zero optical path 74 or the span optical path 76 is aligned with optical path 108. When the optical paths 108 and 74 or 76 are aligned, the axes of the apertures in transducer 100 and calibrator unit 2 are also substantially coincidental.

Flanges 52, grooves 54, and beveled corners 56 of unit 2 and gap 118 of detector housing 102 positively engage to ensure that: (a) the transducer 100 is placed on calibrator unit 2 with the correct orientation, and (b) the optical paths are aligned.

Figure 8:
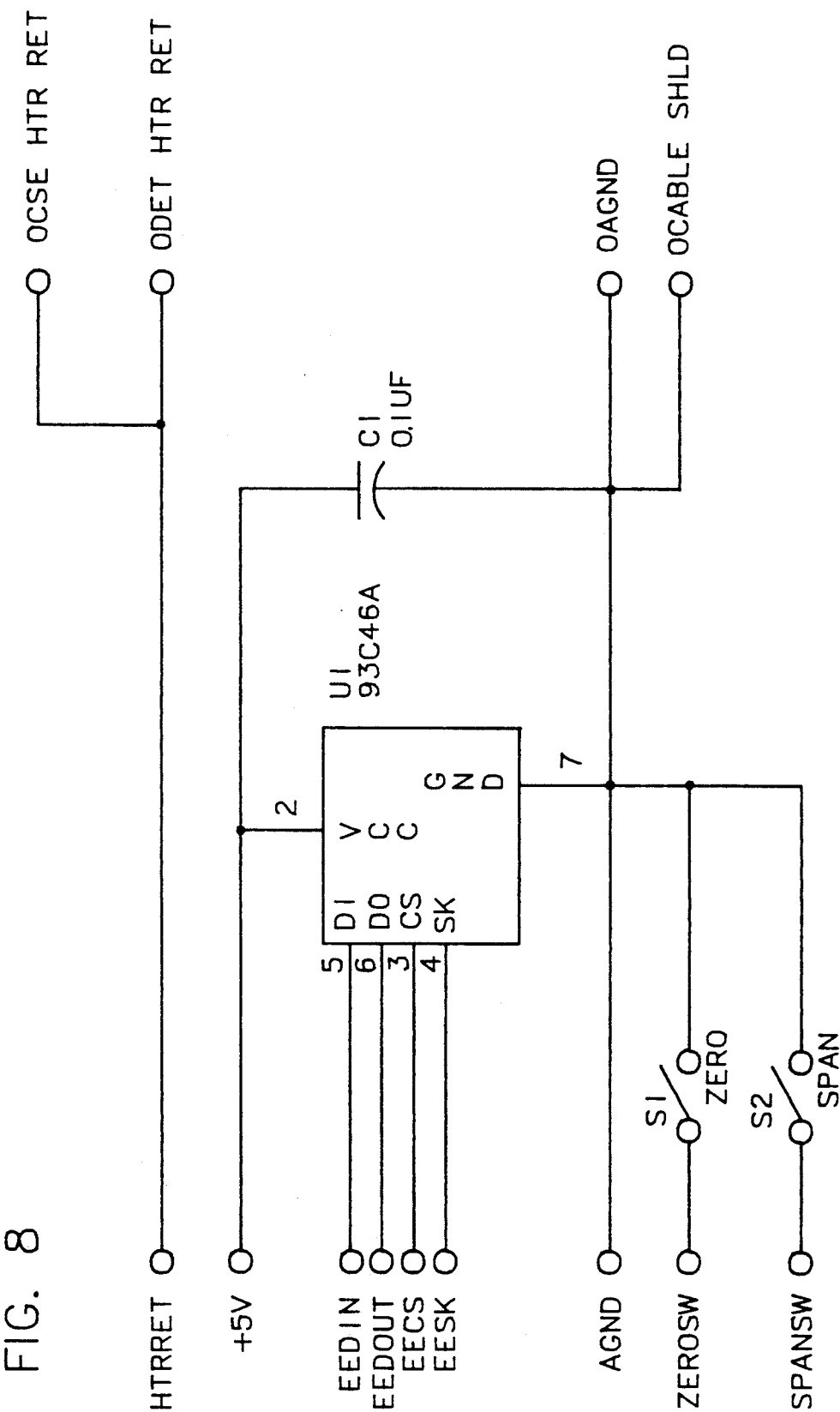
FIG. 8 is a schematic diagram of the printed circuit board in the calibrator unit.

Referring now to FIG. 8, terminals for electrically connecting printed circuit board 82 to a gas analyzer or other control unit via connector 24 are identified by the name of the signals conducted therethrough and are located along the left-hand margin of FIG. 8. Terminals electrically connecting PC board 82 with transducer 100 through external cable 46 are identified by the signals transmitted therethrough and are located along the right-hand margin of FIG. 8.

In the same figure, reference character U1 identifies the EEPROM memory device 88. The EEPROM used in the preferred embodiment is a 93C46A integrated circuit (IC) chip.

A supply voltage of +5 V is applied to terminal 2 of EEPROM U1, and terminal 7 is connected to ground. Capacitor C1 is connected between the +5 V source voltage and ground. It filters out noise on the source voltage line.

Signals EEDIN, EEDOUT, EECS, and EESK are applied to terminals 5, 6, 3, and 4, respectively, of EEPROM U1. Data is written into EEPROM U1 on the EEDIN line connected to terminal 5. Data is read out from terminal 6 of EEPROM U1 via the EEDOUT line connected thereto. Data is preferably written into and read from EEPROM U1 in serial form. The EECS and EESK signals applied to terminals 3 and 4 control the timing and direction of the data flowing into and out of EEPROM U1.

The following is a list of the data stored in EEPROM U1 in that embodiment of the present invention disclosed herein.

The sensor ID number corresponding to the transducer 100 attached to be cell housing Z:
a parameter type;
a reference cell valve (times 10);
the gas calibrated Zero Ratio;
the gas calibrated Span Ratio
the reference used for last calibration
the cell Zero Calibration Valve;
the cell Span Calibration Valve;
the cell data and reference AGC valves;
the cell calibration data and reference signal averages;
the source current valve during cell calibration
the adaptor Zero Calibration Valve;
the adaptor Span Calibration Valve;
the adaptor data and reference AGC valves;
the adaptor calibration data and reference signal averages;
the source current valve during adaptor calibration During the calibration of a transducer, the above-listed data is accessible by the gas analyzer or other unit which controls the calibration process. Accordingly, any value not measured by a detector in unit 106 that is peculiar to the combination of the particular transducer being calibrated and calibrator unit 2 is assumed to be serially read from memory device 88 (EEPROM U1).

System ground enters PC board 82 through terminal AGND and leaves through terminal OAGND.

Zero reed switch S1 (or 84) is connected between the ZEROSW terminal and the system ground. Switch S1 closes when zero cell 78 is placed in the optical path 108 of transducer 100. Similarly, reed Switch S1 closes when zero cell 78 is placed in the optical path 108 of transducer 100. Similarly, reed switch S2 (86), which is connected between terminal SPANSW and system ground, closes when the span cell 80 is placed in the optical path 108 of transducer 100. In the herein disclosed embodiment of the invention a microprocessor in the gas analyzer monitors the ZEROSW signal and SPANSW signals to determine whether the zero cell 78 or span cell 76 is placed in the optical path 108 of transducer 100.

A shield 152 surrounding external cable 46 is connected to the system ground to shield the conductive wires within cable 46 from electromagnetic noise in the environment.

Case and detector heater return signals pass from transducer detector unit 106 through PC board 82, entering through the OCSE HTR RET and ODET HTR RET terminals and leaving through the HTRRET terminal. The case and detector heater systems are disclosed in detail in copending application Ser. No. 425,709, are not by themselves part of the present invention, and will be discussed below only to the extent that they relate to the present invention.

The gas analyzer, which is not shown, typically includes: (a) a keyboard and a display, such as a cathode ray tube (CRT) or liquid crystal display (LCD), which allows the user to enter and receive instructions and data; and (b) a microprocessor which performs calculations, steps through the above-mentioned logic trees, controls the keyboard and display, sends signals to the calibrator unit 2 and transducer 100, and receives signals from the transducer calibrator unit. Except for the steps will be described herein only to the extent necessary for an understanding of the present invention.

The steps performed by the gas analyzer microprocessor in the course calibrating a transducer 100 can best be understood by referring to FIGS. 6 and 7A-D.

Figure 7A:
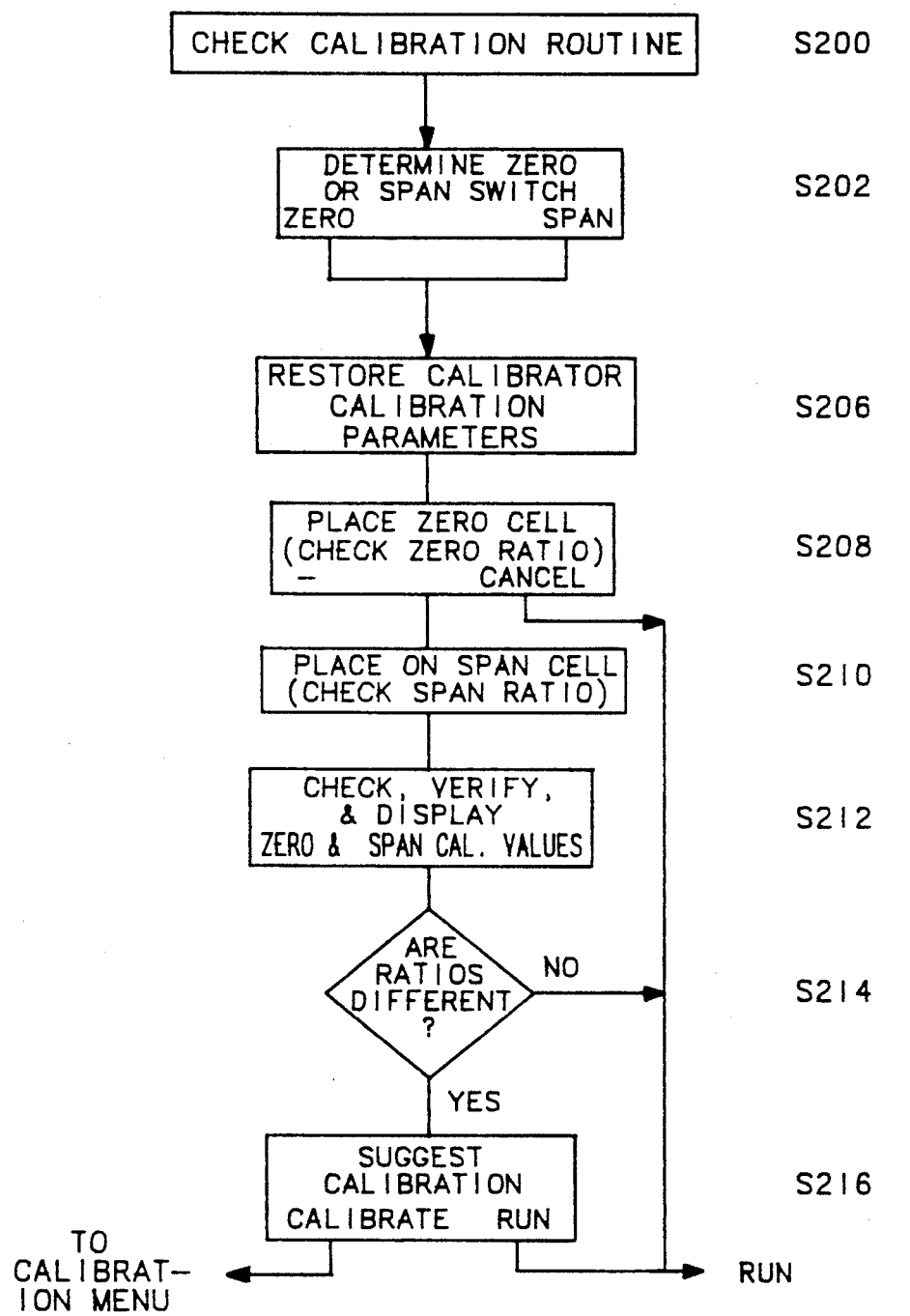
FIG. 7A is a flow chart of a CHECK CALIBRATION PROCEDURE called from the MAIN PROGRAM.

The MAIN CALIBRATION PROGRAM begins at step 100 (FIG. 7A). At step 102, the operator must choose among: (a) operating soft key switches; (b) detecting airway conditions, and (c) performing calibration. If the operator chooses to operate soft key switches or detect airway conditions; the processing proceeds to steps S104 and S106, respectively. The soft key switch and detect airway condition routines of steps S104 and S106 are not in themselves part of the present invention and will not be discussed further herein.

If the operator chooses calibration at step S102, the process moves to step S108, and the operator must choose between: (a) performing a new calibration and (b) checking a previous calibration. If the operator chooses to check a previous calibration, the process goes to the CHECK CALIBRATION ROUTINE of step S200.

If the operator chooses to perform a new calibration, the process moves to step S112. At step S112, the operator is prompted to choose among the following: (a) airway calibration, (b) detector calibration, and (c) exiting the calibration processes and running gas analyzing routines.

If the operator chooses airway calibration, the process moves to the airway calibration routine in step S114. The airway calibration routine is not in If the operator chooses airway calibration, the process moves to the airway calibration routine in step S114. The airway calibration routine is not in itself part of the present invention and will not be discussed further herein.

If the operator chooses detector calibration at step S112, the process moves to step S118, and the operator is presented with a CALIBRATION TYPE menu. The CALIBRATION TYPE menu presents the operator with the following choices: (a) calibrator calibration and (b) gas calibration.

If the operator chooses gas calibration at step S118, the process moves to the GAS CALIBRATION ROUTINE of step S300.

On the other hand, if the operator chooses calibrator calibration, the process moves to step S120 where the operator must choose between: (a) one-step calibration and (b) cell calibration. If the operator chooses one step calibration, the process moves to the ONE-STEP CALIBRATION ROUTINE of step S500. If the operator chooses cell calibration, the CELL CALIBRATION ROUTINE is performed at step S216.

Each relevant routine called by the MAIN CALIBRATION PROGRAM will now be explained in detail with reference to the appropriate Figure of the drawing.

The CHECK CALIBRATION ROUTINE begins at step S200 as shown in FIG. 7A. At step S202 the microprocessor determines whether the zero cell 78 or span cell 80 has been placed in the detector optical path. If the ZEROSW signal is low, zero cell 78 has been placed in the optical path; and, if the SPANSW signal is low, the span cell 80 has been placed in the detector optical path.

After determining which cell is in the detector path, step S200 asks the operator if the adult airway adapter is being used. If it is, the processing goes directly to step S208. If the adult airway adapter is not being used, the processing goes first to step S206 where the parameters for the adult airway adapter are restored for calibration.

The processing then goes to step S208, which instructs the operator to place the zero cell in the detector optical path, if necessary; and a Zero Ratio is determined in the manner described above. The operator has the option of cancelling the calibration check at step S208. Otherwise, the processing steps to step S210.

The operator is instructed at step S210 to place the transducer 100 on the span cell 80, at which time the span ratio is measured. At step S212, the zero and span ratios are displayed; and at step S214 the zero and span ratios calculated at steps S208 and S210 are compared with the zero and span ratios calculated during the last calibration of the gas analyzer unit. If the ratios calculated in steps S208 and steps S210 are different, i.e., greater than or less than the previously calculated ratios by a predetermined amount, the processing moves to step S216 where the operator is prompted to recalibrate.

If, on the other hand, the ratios are not significantly different; i.e., within a predetermined value above or below the previously calculated ratios, the processing continues with normal measurement of gas concentration. At the next step, S216, the operator also has the discretion to continue normal analysis of gas without further calibration.

If at step S216 the operator chooses to calibrate the transducer 100, the processing goes to step S112 where the operator is presented with the calibration menu.

Figure 7B:
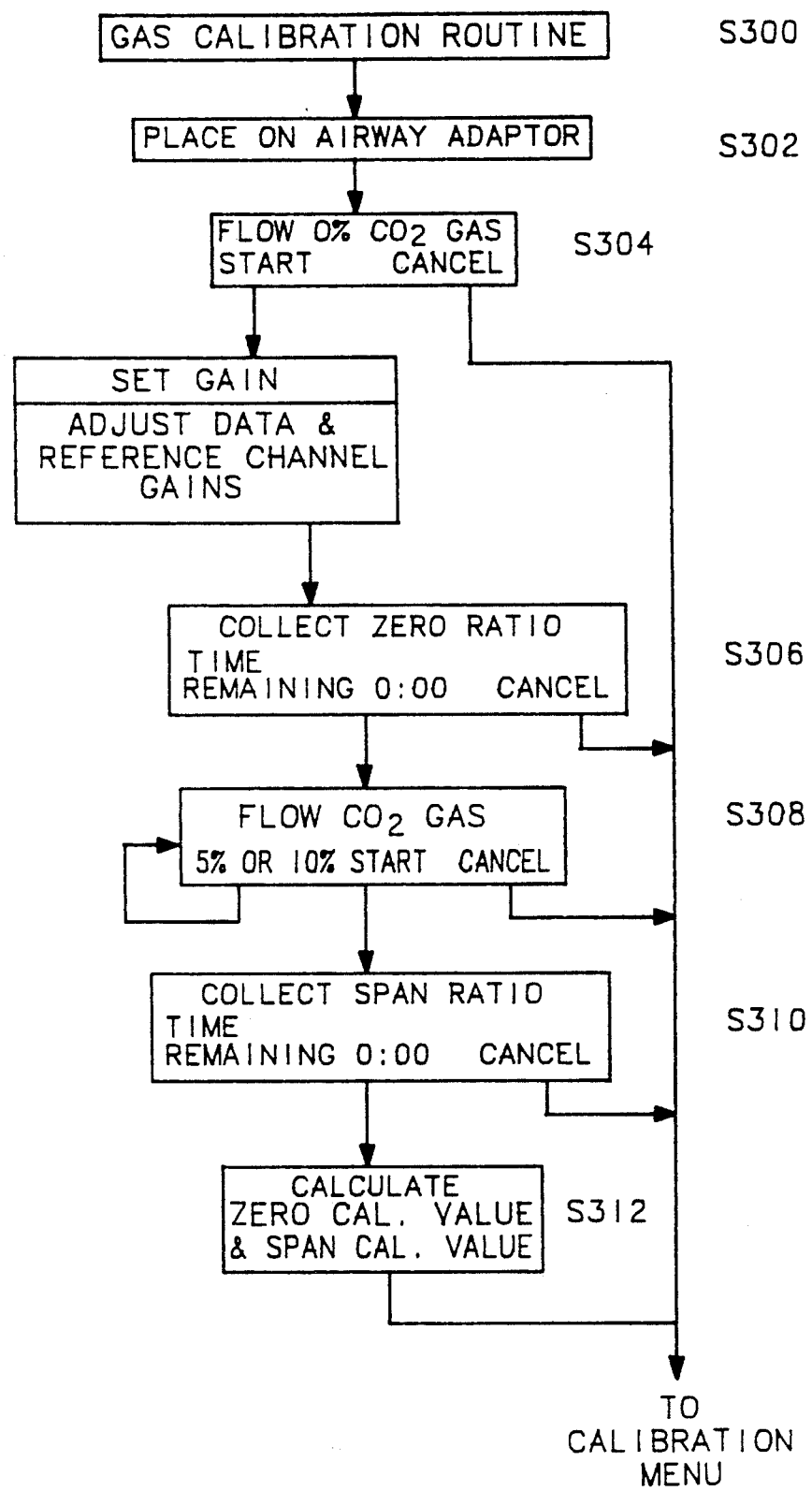
FIG. 7B is a flow chart of a GAS CALIBRATION ROUTINE called from the MAIN PROGRAM.

Referring now to FIG. 7B, the GAS CALIBRATION ROUTINE begins at step S300. Step S302 prompts the operator to assemble transducer 100 to airway adapter 120.

At step S304, the operator is prompted to begin flowing gas with no $CO_2$ through the airway adapter. The operator then enters "start" to proceed with the gas calibration procedure or "cancel" to exit the gas calibration procedure and return to the calibration menu.

If the operator chooses "start", the Zero Ratio is obtained at step S306. More specifically, a clock is set to a predetermined measurement period and then counted down to zero. During the measurement period, plural ratios of the data detector output signal to the reference detector output signal are measured. The average of these ratios is subsequently employed as the Zero Ratio.

The operator may cancel the GAS CALIBRATION PROCEDURE and return to the calibration menu at anypoint during the measurement period.

At step S308 the operator is prompted to flow a gas mixture containing five (or 10) percent $CO_2$ through the airway adapter.

When the operator enters "start" at step S308, the process moves to step S310 where a clock is again set to a measurement value and counted down to zero. Plural ratios of the data detector output to the reference detector output are taken during the countdown of the clock. The average of these ratios is used as the Span Ratio. Again, the operator has the option to cancel the GAS CALIBRATION ROUTINE and return to the calibration menu during the measurement period of step S310.

When the clock reaches zero at step S310, the process moves to step S312, where the Zero Cal Factor and Span Cal Factor are calculated from the Zero Ratio and Span Ratio according to equations (6) and (7). The process then returns to the calibration menu.

The ONE STEP CALIBRATION PROCEDURE begins at step 400 (see FIG. 7C). At step S402, the operator is prompted to place transducer 100 on the zero cell 78 of calibrator 2. At step S404 a clock is set to a predetermined measurement value and counted down to zero. During the period in which the clock is counting down, ratios of the data and reference detector output signals are calculated at different points in time. The average is taken as the New Zero Ratio. The operator has the option to cancel the ONE STEP CALIBRATION PROCEDURE during step S404 and return to the calibration menu.

After the clock counts down to zero, the process goes to step S406. At step S406, the Zero and Span Cal Values are calculated according to equations (6) and (7) from: (a) the New Zero Ratio collected at step S404 and (b) the New Span Ratio calculated from the Concentration Factor stored in memory device 88 (EEPROM U1) and the New Zero Ratio according to equations (10) or (11).

The operator is prompted to place the transducer 100 on span cell 80 of calibrator 2 at step S408.

The process then proceeds to step S410, at which point the clock is again set to a measurement value. The clock is then counted down to zero, and the ratios of data and reference detector output signals are generated at different points. The operator has the option to cancel the one-step calibration procedure during step S408 and return to the calibration menu.

After the clock counts down to zero, the average of the ratios calculated during the measurement period is taken. A verification Span Ratio is the average of these ratios.

A verification Span Cal Value is calculated at step S412 from the verification Span Ratio collected at step S410 and the New Zero Ratio collected at step S404 according to equation (7).

At step S414, the Span Cal Value calculated at step S406 is compared with the verification Span Cal Value generated at step S412 from the New Zero and Measured Span Ratios. If the Span Cal Value calculated at step S406 is within a sufficiently small range of the verification Span Cal Value calculated at step S412: (a) the Span Cal Value calculated at step S406 is determined to be good at step S416; and (b) the process exits the ONE-STEP CALIBRATION ROUTINE to the calibration menu.

If, on the other hand, the Span Cal Value calculated at step S406 is not within a sufficiently small range of the Verification Span Value calculated at step S402: (a) the span value calculated at S406 is determined not to be good, and (b) the process proceeds to step S418.

If the Span Cal Value calculated at step S404 has been determined not to be good for the first time at step S418, the operator is given the opportunity at step S418 to recalculate the Zero and Span Cal Values by returning to step S402. The operator may also elect to return to the calibration menu without repeating the ONE-STEP CALIBRATION PROCEDURE.

Figure 7D:
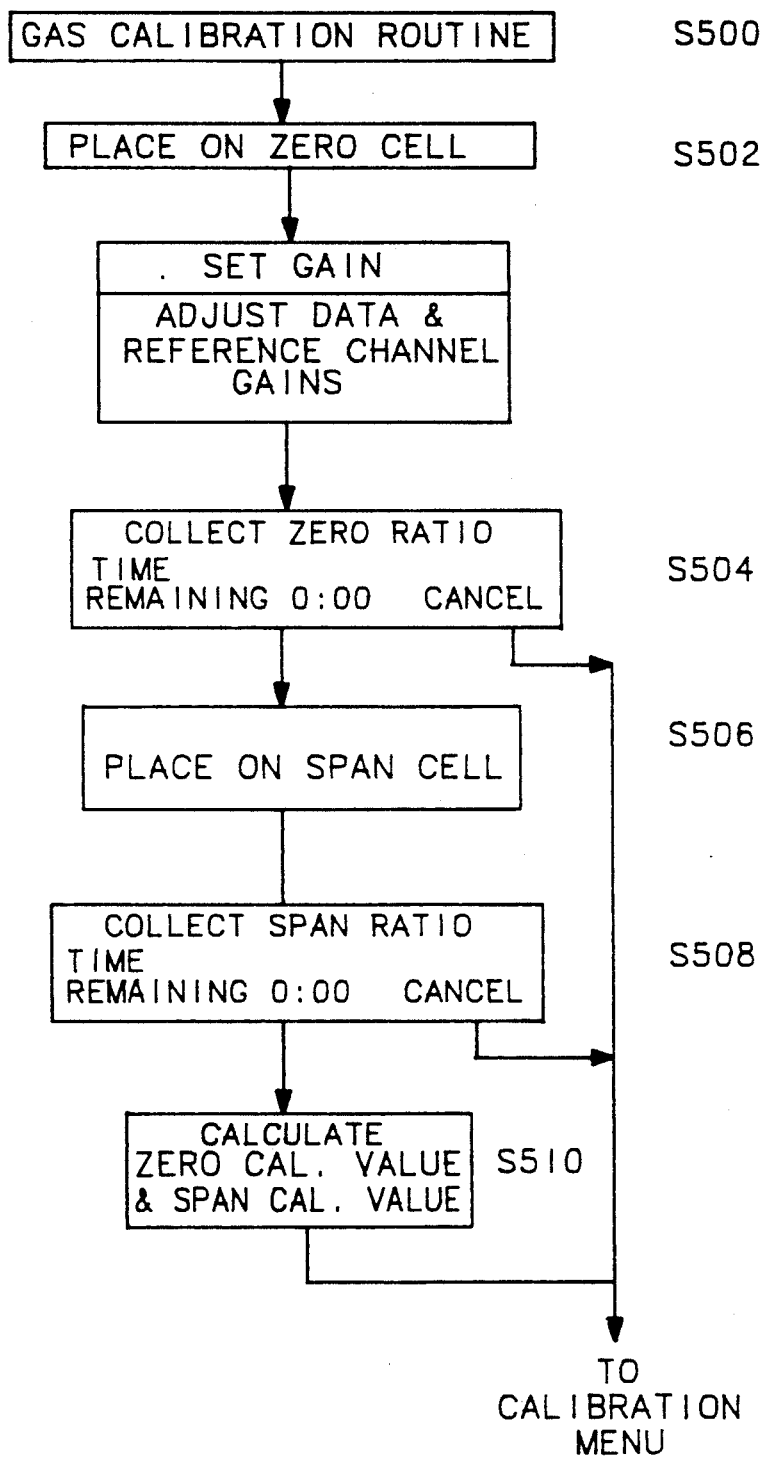
FIG. 7D is a flow chart depicting a CELL CALIBRATION ROUTINE of the calibration procedure.

The CELL CALIBRATION ROUTINE begins at step S500 (see FIG. 7D). At step S502, the operator is prompted to place transducer 100 on the zero cell 78 of calibrator 2. The process then proceeds to step S504 where a clock is set to a measurement value and then counted down to zero. While the clock is counting down to zero, the operator may choose to cancel the CELL CALIBRATION ROUTINE and return to the calibration menu.

Ratios of the data and reference detector output signals are generated at different points in time during the countdown of the clock. The Zero Ratio is the average of the different ratios and is calculated after the clock reaches zero.

The process then proceeds to step S506, and the operator is prompted to place the transducer 100 on the span cell 80 of calibrator 2. The process then proceeds to step S508 at which point the clock is again set and begins counting down. The operator is given the opportunity to cancel the CELL CALIBRATION ROUTINE at step S508 and return to the calibration menu at step S112.

When the clock reaches zero, the Span Ratio is calculated. It is the average of ratios of the data and reference detector output signals taken while the clock is counting down to zero.

If the operator does not choose to cancel the cell calibration routine at step 508, the routine proceeds to step S510. In this step the Zero Cal Factor and Span Cal Factor are calculated from the Zero Ratio and Span Ratio according equations (6) and (7).

It will be clear to one of ordinary skill in the art that many modifications and alterations of the above-discussed representative embodiment may be made without departing from the spirit of the present invention. For example, in the disclosed embodiment, the Concentration Factor is stored as a Zero Ratio and a Span Ratio calculated under the controlled conditions of a factory. Alternatively, the concentration factor may be calculated at the factory and stored in non-volatile memory for later use in calculating the Zero and Span Cal Values.

Additionally, in the disclosed embodiment, the Concentration Factor is stored in an EEPROM mounted on a printed circuit board within the calibrator unit. In some situations, it may be preferable to store the Concentration Factor with the transducer for which it is obtained or in the gas analyzer or other controlling unit in which case it can later be associated with the transducer for which it was calculated.

The specific calibrating unit disclosed herein may also be radically changed and still come within the scope of the present invention. For example, a span cell filled with a known concentration of the designated gas can be substituted for the above-described span cell.

The invention may be embodied in still other forms without departing from the spirit or essential characteristics of the invention. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed is:

1. The combination of:
   a transducer having: (a) a source for generating a beam of infrared radiation and propagating the beam along an optical path through a gas sample, and (b) a detector spaced along the optical path, from said source, for generating a signal which is indicative of the attenuation of the beam by a designated gas in said sample and, consequentially, of the concentration of the designated gas;
   memory means for storing a predetermined concentration factor for said transducer, the concentration factor being indicative of the magnitude of the signal generated by the detector for a known concentration of the designated gas;

calibration means for calculating calibration values for said transducer from: (a) the concentration factor, and (b) a zero signal generated by the detector when the designated gas is absent; and concentration calculation means for subsequently calculating the concentration of the designated gas in the sample from: (a) the calibration values, and (b) the magnitude of the signal generated by the detector as the beam of infrared radiation traverses the sample.

2. A combination as defined in claim 1, in which the memory means is non-volatile and physically connected to the calibration unit.

3. A combination as defined in claim 1, further comprising a cable electrically connecting the transducer to the calibration means.

4. A combination as defined in claim 1, further comprising means for checking the calibration values generated by the calibration means with a span signal generated for a known, span concentration of the designated gas.

5. A combination as defined in claim 4, in which the means for checking the calibration values comprises a span cell with an energy reflecting or absorbing material corresponding to the span concentration of the designated gas, said span cell being locatable in the optical path of the transducer to obtain the span signal.

6. A combination as defined in claim 5, in which the span cell has two transparent windows formed of optically transparent material, said windows being alignable along said optical path.

7. A combination as defined in claim 5, in which the energy reflecting or absorbing material is formed in a layer on the surfaces of at least one of said span cell windows.

8. A combination as defined in claim 5, in which the energy reflecting or absorbing material is a disk located between the two windows.

9. A combination as defined in claim 6, in which the window material is sapphire.

10. A combination as defined in claim 1, in which the calibration means calculates calibration values according to the following instructions:

$$ZCV = NZR, \text{ and}$$

$$SCV = \frac{IX_S}{NZR - NSR}$$

where ZCV is the Zero Cal Value, NZR is the signal generated by the detector when the designated gas is absent during a calibration procedure, SCV is the Scan Cal Value, NSR is the NZR multiplied by the concentration factor, and $IX_S$ is an index value that cross-references the span concentration level to a substantially equal concentration level stored in a table relating signals generated by the detector to concentration levels.

11. A combination as defined in claim 1, in which the calibrating means further comprises:

a magnet;

a zero cell and a span cell; and zero and span cell reed switches so located relative to the zero and span cells that the zero cell reed switch is operated by the magnet when the zero cell is in the optical path and the span cell reed switch is operated by the magnet when the span cell is in the optical path.

12. A combination as defined in claim 1 in which:

the transducer includes a housing having: (a) two zero apertures formed therein and aligned along a zero optical path through the housing, and (b) two span apertures formed therein and aligned along a span optical path through the housing and windows spanning the zero and span apertures to keep foreign matter from the interior of the housing while transmitting infrared radiation along the optical paths without significant attenuation; and said memory means is of the non-volatile type and is located in said housing.

13. A combination as defined in claim 12 in which the transducer has reflecting or absorbing material for attenuating infrared radiation passing through the span apertures along with span optical path.

14. A combination as defined in claim 12 in which said reflecting or absorbing material is formed in a layer on the surfaces of at least one window covering a span aperture.

15. A combination as defined in claim 12 in which the memory means is mounted on a printed circuit board in the housing.

16. A combination as defined in claim 1 in which the concentration calculation means calculates the concentration of the specimen of the designated gas according to the following equations:

$$IX = SCV(ZCV - MR), \text{ and}$$

$$CONC = \text{TABLE}\,[IX]$$

where MR is the measured signal, IX is an index value that cross-references the measured signal to a corresponding concentration value stored in a table relating signals generated by the detector to concentration levels, SCV is the Scan Cal Value, ZCV is the Zero Cal Value, CONC is the concentration of the designated gas in the sample gas, and TABLE is an empirically generated table relating IX values to CONC values.

17. A combination as defined in claim 1, in which the calibration means comprises: a calibration unit including a zero cell which does not contain the designated gas and can be placed in the optical path between the infrared radiation source and the detector to produce the zero signal.

18. A method of calibrating an infrared radiation transducer from: (a) the magnitude of a beam of infrared radiation after that radiation has been attenuated by a specimen of a designated gas, and (b) calculated calibration values, said method comprising the steps of:

generating a concentration factor for the transducer which is to be calibrated, said concentration factor being indicative of the magnitude of the infrared radiation beam as attenuated by a known concentration of the designated gas;

storing the concentration factor in a non-volatile memory associated with said transducer;

calculating calibration values from: (a) the concentration factor, and (b) a value reflecting the magnitude of the unattenuated infrared radiation beam.

19. A method of calibrating a transducer as defined in claim 18, further comprising the steps of:

measuring a span level of the infrared radiation beam as attenuated by a known span concentration of the designated gas;

calculating a concentration level of the designated gas from the span concentration level and the calibration values; and comparing the calculated concentration level with the span concentration level to verify the accuracy of the calibration values calculated from the concentration factor and the unattenuated level of the infrared radiation beam.

20. A method as defined in claim 18, in which the concentration factor ($CF_s$) is calculated by the equation $$CF_S = \frac{SR}{ZR}$$

where ZR is the signal generated by a detector or in the transducer being calibrated in the absence of the designated gas and SR is the signal generated by the detector for a known span concentration level of the designated gas.

21. A method as defined in claim 18, in which the calibration factors are calculated by the equations:

$$ZCV = NZR, \text{ and}$$

$$SCV = \frac{IX_S}{NZR - NSR}$$

where ZCV is the Zero Cal Value, NZR is the signal generated by a detector in the transducer being calibrated when the designated gas is absent during a calibration procedure, SCV is the Scan Cal Value, SR is the signal NZR multiplied by the concentration factor, and $IX_s$ is an index value that cross-references the span concentration level to a substantially equal concentration level stored in a table relating signals generated by the detector to concentration levels.

22. A method as defined in claim 18, in which the concentration factor is determined under controlled conditions using: (a) an infrared radiation source and detector of the transducer, and (b) a known concentration of the designated gas.

23. The method as defined in claim 18, in which the concentration of the designated gas in the sample is calculated according to the following equations:

$$IX = SCV(ZCV - MR), \text{ and}$$

$$CONC = TABLE\ [IX]$$

where MR is the measured signal, IX is an index value that cross-references the measured signal to a corresponding concentration value stored in a table relating signals generated by the detector to concentration levels, SCV is the Scan Cal Value, ZCV is the Zero Cal Value, CONC is the concentration of the designated gas in the sample gas, and TABLE is an empirically generated table relating IX values with CONC values.

* * * * *